United States Patent [19]

Papenfuhs et al.

[11] Patent Number: 5,233,083
[45] Date of Patent: Aug. 3, 1993

[54] PROCESS FOR THE PREPARATION OF 2-AMINO-3-CHLOROBENZOIC ACID

[75] Inventors: Theodor Papenfuhs; Jochen Rapp, both of Frankfurt am Main, Fed. Rep. of Germany

[73] Assignee: Hoechst Aktiengesellschaft, Frankfurt am Main, Fed. Rep. of Germany

[21] Appl. No.: 929,722

[22] Filed: Aug. 13, 1992

[30] Foreign Application Priority Data

Aug. 16, 1991 [DE] Fed. Rep. of Germany ....... 4127150

[51] Int. Cl.$^5$ .............................................. C07C 63/04
[52] U.S. Cl. ................................................... 562/456
[58] Field of Search ......................................... 562/456

[56] References Cited

U.S. PATENT DOCUMENTS

| | | | |
|---|---|---|---|
| 4,990,661 | 2/1991 | Petersen et al. | 562/456 |
| 4,990,663 | 2/1991 | Chang et al. | 562/456 X |
| 5,068,392 | 11/1991 | McKendry et al. | 562/456 X |

*Primary Examiner*—Arthur C. Prescott
*Attorney, Agent, or Firm*—Connolly and Hutz

[57] ABSTRACT

The present invention relates to a process for the preparation of 2-amino-3-chlorobenzoic acid by dissolving 1 mol of 2,3-dichlorobenzoic acid in about 400 to about 2000 parts of water with at least the equimolar amount of an alkali metal hydroxide or with an aqueous solution of the equimolar amount of an alkali metal hydroxide, and subsequently reacting it with about 500 to about 2500 mol % of ammonia at temperatures of about 150° to about 220° C. in the presence of copper bronze, copper(I) salts and/or copper(II) salts.

12 Claims, No Drawings

PROCESS FOR THE PREPARATION OF 2-AMINO-3-CHLOROBENZOIC ACID

The invention relates to an improved process for the preparation of 2-amino-3-chlorobenzoic acid by a chlorine/ammonia exchange reaction (ammonolysis reaction) on 2,3-dichlorobenzoic acid using aqueous ammonia in the presence of copper-containing catalysts, the reaction being carried out at elevated temperatures and under pressure. The process gives 2-amino-3-chlorobenzoic acid in a high yield and very high industrial purity.

2-Amino-3-chlorobenzoic acid is an important intermediate product for the preparation of pharmaceutical products and for agriculture. 2-Amino-3-chlorobenzoic acid is a precursor for 4-chloro-11-oxo-11H-pyrido-[2,1-b]quinazoline-8-carboxylic acid, a quinazoline derivative which is used pharmaceutically as an antiallergic agent (DE 28 12 586 A1). As a precursor for thiazolo-[2,3-b]-quinazolones, 2-amino-3-chlorobenzoic acid is used in regulators for plant growth (DE 31 42 727 A1).

2-amino-3-chlorobenzoic acid has hitherto been prepared, for example, by reduction of 3-chloro-2-nitrobenzoic acid with sodium dithionite in aqueous ammonia (U.S. Pat. No. 4,347,246); by reduction of 3-chloro-2-nitrobenzoic acid with hydrogen gas over platinum catalysts (D. Pressman et al., Am. Soc. 76 [1954]6336, 6337), or by reduction with sodium borohydride in methanol in the presence of $NiCl_2 \cdot 6H_2O$ (JP 01299259). A disadvantage of all the preparation methods described above is that they are all based on 3-chloro-2-nitrobenzoic acid, which is of quite difficult accessibility Another preparation method starts from 7-chloro-indoline-2,3-dione, reaction of which with hydrogen peroxide solution in aqueous sodium hydroxide solution leads to 3-chloroanthranilic acid (B. R. Baker et al., J. org. Chem. 17 [1952]141, 143; P. W. Sadler, R. L. Warren, Am. Soc. 78 [1956]1251, 1254). A particular disadvantage of this synthesis route is that the condensation of o-chloroaniline, chloral and hydroxylamine gives 7-chloro-indoline-2,3-dione (7-chloroisatin) in a yield of only 35% of theory, and hydrolysis of 7-chloroisatin gives 3-chloroanthranilic acid in a yield of only 78% of theory (27.3% overall yield over both stages). An alternative process, Hoffmann degradation of 3-chlorophthalamic acid, gives 47% of theory of 2-amino-3-chlorobenzoic acid (G. S. Patel et al., J. Indian Chem. Soc. 34 [1957]373).

The low yields of the known processes mentioned above as examples and also the nonexistent availability of the starting compounds of difficult accessibility render industrial preparation impossible from ecological and economic aspects.

There was therefore a need for an improved industrial process for the preparation of 2-amino-3-chlorobenzoic acid which, using readily accessible and industrially available starting compounds gives, in one process stage, a product which can be isolated in a high purity and high yields and if possible by simple filtration.

It has now been found, surprisingly, that 2-amino-3-chlorobenzoic acid can be prepared in a high yield and a very high industrial purity by dissolving 1 mol of 2,3-dichlorobenzoic acid in about 400 to about 2000 parts of water with at least the equimolar amount of an alkali metal hydroxide, and then reacting it with about 500 to about 2500 mol % of ammonia at temperatures of about 150° to about 220° C., preferably about 160° to about 190° C., particularly preferably about 165° to about 175° C. If an aqueous ammonia solution is used, a commercially available 25% strength solution, for example, can be employed. However, if desired, an additional amount of ammonia can be introduced into such a solution, the upper limit being an approximately 60% strength aqueous solution. The use of an aqueous ammonia solution, the ammonia content of which is considerably less than 25%, is not advisable because an undesirable lengthening of the reaction time and a reduced space/time yield would be associated with this.

Possible alkali metal hydroxides are the hydroxides of lithium, sodium, potassium, rubidium or cesium. Potassium hydroxide is preferably used, and sodium hydroxide is particularly preferred. The alkali metal hydroxides can be employed in solid form or in the form of an aqueous solution. If solutions of the alkali metal hydroxides are employed, the amount of water in the process is reduced accordingly.

In the process according to the invention, the 2,3-dichlorobenzoate (1 mol) primarily formed is advantageously reacted in about 400 to about 2000 parts of water, preferably in about 450 to about 1500 parts of water, particularly preferably in about 500 to about 600 parts of water, with about 500 to about 2500 mol % of ammonia, preferably with about 780 to about 1550 mol % of ammonia, particularly preferably with about 1200 to about 1300 mol % of ammonia, it being possible for the 2,3-dichlorobenzoate to be present as a solution or suspension in the water at the start of the process. The ammonia can be added in the liquid or gaseous form or in the form of concentrated aqueous solutions. If concentrated aqueous ammonia solutions are used, the amount of water is to be reduced accordingly.

Copper catalysts which can be used are copper bronze, copper(I) and/or copper(II) salts, such as, for example, the halides, such as, for example, the chlorides, or the oxides, nitrates, sulfates, carbonates or acetates of 1- or 2-valent copper, or mixtures thereof. Copper(I) chloride is preferably used. The copper catalysts are appropriately employed in an amount of about 20 mol %, preferably about 5 mol %, based on the 2,3-dichlorobenzoic acid. Copper(I) chloride is preferably employed in a proportion of about 2 to about 20 mol %, particularly preferably about 1.8 to about 5 mol %.

In the reaction temperature ranges mentioned above, a pressure of about 20 to about 60 bar is established, and for this reason the reaction is appropriately or necessarily carried out in an autoclave.

The reaction takes between about 30 minutes and about 10 hours, usually between about 1 and about 3 hours. When the reaction has ended, the excess ammonia is recovered by distillation and recycled. The product is precipitated by acidifying the bottom product to pH 3–4 with concentrated hydrochloric acid or sulfuric acid. The product is then collected and washed with water.

The following examples serve to illustrate the process, without limiting it thereto. Parts denote parts by weight.

EXAMPLE 1

191 parts of 2,3-dichlorobenzoic acid, 80 parts of 50% strength aqueous sodium hydroxide solution, 1004 parts of 25% strength aqueous $NH_3$ solution and 5 parts of CuCl are initially introduced into a 2 l V4A autoclave. 89 parts of liquid $NH_3$ ($d_{20}$: 0.61) are also forced in, and the autoclave is heated at 170° C. for 5 hours, during which the pressure drops from initially 25 bar to about 22 bar. When the reaction has ended, the contents of the autoclave are cooled to 25° C. and the autoclave is emptied via the ascending line. The reaction solution is boiled under reflux until a bottom temperature of 100° C. is reached, and the NH$_3$ gas driven off is collected in a waste gas washer. After cooling to 25° C., the reaction solution is brought to pH 3 with 122 parts of 30% hydrochloric acid. The 2-amino-3-chlorobenzoic acid which has precipitated is filtered off with suction, washed with 300 parts of water and dried at 80° C. in vacuo. 145 parts (85% of theory) of 2-amino-3-chlorobenzoic acid of melting point 185° to 187° C. are obtained.

If, instead of 5 parts of CuCl, 10 parts of Cu(OH)$_2$.2H$_2$O or 8 parts of CuCl$_2$.2H$_2$O are used and the procedure is otherwise as described above, practically the same result is obtained.

EXAMPLE 2

A solution comprising 191 parts of 2,3-dichlorobenzoic acid and 40 parts of NaOH prills in 500 parts of water, and 3 parts of CuCl are initially introduced into a 2 l V4A autoclave. 425 parts of liquid NH$_3$ (d$_{20}$: 0.61) are then also forced in, and the autoclave is heated at 165° to 175° C. for 3 hours, during which the pressure drops from initially 50 bar to about 46 bar. When the reaction has ended, the contents of the autoclave are cooled to 25° C. and drained off over the ascending line. The reaction solution is boiled under reflux until a bottom temperature of 100° C. is reached, and the NH$_3$ gas driven off is collected in a waste gas washer. Working up in accordance with Example 1 gives 168 parts (98% of theory) of 2-amino-3-chlorobenzoic acid of melting point 185° to 187° C.

If, instead of 3 parts of CuCl, 6 parts of copper bronze or 5 parts of CuCl$_2$.2H$_2$O are used and the procedure is otherwise as described above, practically the same result is obtained.

We claim:

1. A process for the preparation of 2-amino-3-chlorobenzoic acid, which comprises dissolving 1 mol of 2,3-dichlorobenzoic acid in about 400 to about 2000 parts of water with at least the equimolar amount of an alkali metal hydroxide or with an aqueous solution of the equimolar amount of an alkali metal hydroxide, and subsequently reacting it with about 500 to about 2500 mol % of ammonia at temperatures from about 150° to about 220° C. in the presence of copper bronze, copper(I) salts and/or copper(II) salts.

2. A process as claimed in claim 1, wherein the reaction is carried out at temperatures of about 160° to about 190° C.

3. A process as claimed in claim 1, wherein the reaction is carried out at temperatures of about 165° to about 175° C.

4. The process as claimed in claim 1,
    wherein the reaction is carried out in the presence of halides, oxides, nitrates, sulfates, carbonates or acetates of 1- or 2-valent copper or mixtures thereof as catalysts.

5. The process as claimed in claim 1,
    wherein the reaction is carried out in the presence of copper(I) chloride as the catalyst.

6. The process as claimed in claim 1,
    wherein the reaction is carried out with about 780 to about 1550 mol % of ammonia.

7. The process as claimed in claim 1,
    wherein the reaction is carried out with about 1200 to about 1300 mol % of ammonia.

8. The process as claimed in claim 1,
    wherein sodium hydroxide or potassium hydroxide is used a the alkali metal hydroxide.

9. The process as claimed in claim 1,
    wherein the 2,3-dichlorobenzoic acid is dissolved in about 450 to about 1500 parts of water with the alkali metal hydroxide.

10. The process as claimed in claim 1,
    wherein the 2,3-dichlorobenzoic acid is dissolved in about 500 to about 600 parts of water with the alkali metal hydroxide.

11. The process as claimed in claim 1,
    wherein the ammonia is used in the liquid or gaseous form or in the form of concentrated aqueous solutions.

12. The process of preparation as claimed in claim 1, wherein said process is a batch process, and, when the reaction has ended and a batch of the 2-amino-3-chlorobenzoic acid product has been prepared, the excess ammonia is recovered by distillation and is used for a batch.

* * * * *